US012635889B2

(12) United States Patent
Hagman et al.

(10) Patent No.: US 12,635,889 B2
(45) Date of Patent: May 26, 2026

(54) DISTANCE COMPENSATION FOR THERMAL IMAGING TEMPERATURE MEASUREMENT OF INNER CANTHUS SYSTEMS AND METHODS

(71) Applicant: FLIR Systems AB, Täby (SE)

(72) Inventors: Henning Hagman, Täby (SE); Tien C. Nguyen, Täby (SE); Petra Maretic, Täby (SE); Katrin Strandemar, Täby (SE)

(73) Assignee: FLIR Systems AB, Täby (SE)

( * ) Notice: Subject to any disclaimer, the term of this patent is extended or adjusted under 35 U.S.C. 154(b) by 573 days.

(21) Appl. No.: 18/145,779

(22) Filed: Dec. 22, 2022

(65) Prior Publication Data

US 2023/0126197 A1      Apr. 27, 2023

Related U.S. Application Data

(63) Continuation of application No. PCT/US2021/039267, filed on Jun. 25, 2021.

(Continued)

(51) Int. Cl.
*A61B 5/01*          (2006.01)
*A61B 3/14*          (2006.01)
(Continued)

(52) U.S. Cl.
CPC .................. *A61B 5/01* (2013.01); *A61B 3/14* (2013.01); *A61B 5/0077* (2013.01);
(Continued)

(58) Field of Classification Search
CPC .... G01J 5/0025; G01J 5/48; G01J 5/80; G01J 2005/0077; H04N 23/23; A61B 5/6844;
(Continued)

(56) References Cited

U.S. PATENT DOCUMENTS 10,598,550 B2 * 3/2020 Christel ............... H04N 25/671
2007/0242856 A1 * 10/2007 Suzuki ................. G06V 40/171
382/103

(Continued)

FOREIGN PATENT DOCUMENTS

| CN | 103026192 A | 4/2013 | |
| CN | 109419495 A | 3/2019 | |
| GB | 2571379 A * | 8/2019 | ............... G06T 7/11 |

OTHER PUBLICATIONS

Church et al., "Influence of environmental factors on infrared eye temperature measurements in cattle," Research in Veterinary Science, Nov. 2013, pp. 220-226, vol. 96, No. 1, Elsevier Ltd., Canada.

*Primary Examiner* — Peter J Macchiarolo
*Assistant Examiner* — Mireille S Sadate-Moualeu
(74) *Attorney, Agent, or Firm* — Haynes and Boone, LLP

(57)          ABSTRACT

Various techniques are disclosed to provide for improved human body temperature detection using thermal images of an inner canthus. In one example, a method includes capturing a thermal image of a human being using a thermal imager. The method also includes determining an uncompensated temperature measurement associated with an inner canthus of a face of the human being using corresponding pixels of the thermal image. The method also includes determining a correction term as a function of a distance between the thermal imager and the human being. The method also includes applying the correction term to the uncompensated temperature measurement to provide a corrected temperature measurement associated with the inner canthus to compensate for attenuation associated with the distance. Additional methods and systems are also provided.

20 Claims, 11 Drawing Sheets

Related U.S. Application Data

(60) Provisional application No. 63/158,273, filed on Mar. 8, 2021, provisional application No. 63/044,516, filed on Jun. 26, 2020.

(51) Int. Cl.

| | |
|---|---|
| *A61B 5/00* | (2006.01) |
| *G01J 5/00* | (2022.01) |
| *G01J 5/48* | (2022.01) |
| *G01J 5/80* | (2022.01) |
| *G06T 7/62* | (2017.01) |
| *G06V 10/74* | (2022.01) |
| *G06V 40/16* | (2022.01) |
| *G16H 30/40* | (2018.01) |
| *H04N 23/23* | (2023.01) |

(52) U.S. Cl.
CPC .......... *A61B 5/7203* (2013.01); *A61B 5/7246* (2013.01); *A61B 5/7264* (2013.01); *A61B 5/7282* (2013.01); *A61B 5/743* (2013.01); *G01J 5/0025* (2013.01); *G01J 5/48* (2013.01); *G01J 5/80* (2022.01); *G06T 7/62* (2017.01); *G06V 10/761* (2022.01); *G06V 40/161* (2022.01); *G16H 30/40* (2018.01); *H04N 23/23* (2023.01); *A61B 2560/0431* (2013.01); *A61B 2576/02* (2013.01); *G01J 2005/0077* (2013.01); *G06T 2207/20084* (2013.01); *G06T 2207/30041* (2013.01); *G06T 2207/30201* (2013.01)

(58) Field of Classification Search
CPC ..... A61B 5/7203; A61B 5/743; A61B 5/6821; A61B 5/7246; A61B 5/0077; A61B 5/7264; A61B 5/7282; A61B 3/14; A61B 5/01; A61B 2576/02; A61B 2560/0431; G06V 10/761; G06V 40/161; G16H 30/40; G06T 7/62; G06T 2207/30041; G06T 2207/30201; G06T 2207/20084
See application file for complete search history.

(56) References Cited

U.S. PATENT DOCUMENTS

| | | | |
|---|---|---|---|
| 2012/0320189 A1* | 12/2012 | Stuart ................... | G01J 5/0265 348/E5.09 |
| 2013/0215928 A1* | 8/2013 | Bellifemine ............. | G01J 5/02 374/121 |
| 2015/0009335 A1 | 1/2015 | Strandemar | |
| 2016/0113517 A1* | 4/2016 | Lee ...................... | H04N 23/811 600/474 |
| 2020/0175255 A1 | 6/2020 | Kücükcayir et al. | |
| 2021/0396586 A1* | 12/2021 | Price ................... | A61B 5/4887 |

\* cited by examiner

800

900

1000

1100

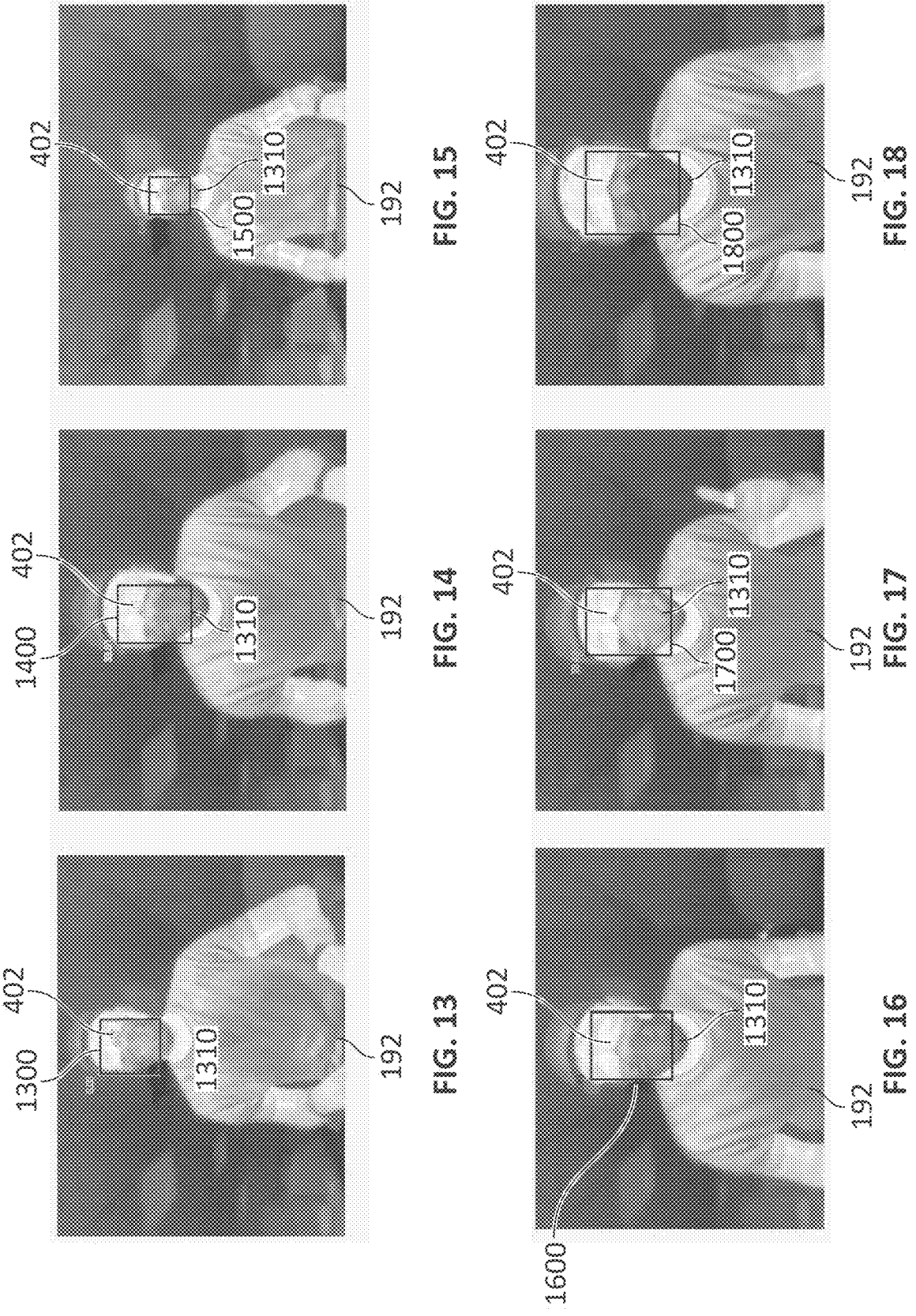

DISTANCE COMPENSATION FOR THERMAL IMAGING TEMPERATURE MEASUREMENT OF INNER CANTHUS SYSTEMS AND METHODS

CROSS-REFERENCE TO RELATED APPLICATIONS

This application is a continuation of International Patent Application No. PCT/US2021/039267 filed Jun. 25, 2021 and entitled "DISTANCE COMPENSATION FOR THERMAL IMAGING TEMPERATURE MEASUREMENT OF INNER CANTHUS SYSTEMS AND METHODS," which claims priority to and the benefit of U.S. Provisional Patent Application No. 63/044,516 filed Jun. 26, 2020 and entitled "DISTANCE COMPENSATION FOR THERMAL IMAGING TEMPERATURE MEASUREMENT OF INNER CANTHUS SYSTEMS AND METHODS," and U.S. Provisional Patent Application No. 63/158,273 filed Mar. 8, 2021 and entitled "THERMAL IMAGING TEMPERATURE MEASUREMENT OF INNER CANTHUS SYSTEMS AND METHODS," all of which are hereby incorporated by reference in their entirety.

TECHNICAL FIELD

The present invention relates generally to thermal imaging and, more particularly, to compensating for distance-related attenuation of thermal image temperature measurements and detecting a face and an inner canthus of a human being.

BACKGROUND

Thermal imaging systems are frequently used to detect the temperatures of various objects or persons in a scene. For example, in the case of human beings, such systems may be used to detect body temperature. Such systems can be particularly useful in the detection of elevated body temperatures associated with possible health conditions (e.g., infections or disease).

In some cases, an inner canthus of the human eye (e.g., the inner corner of the eye where the upper and lower lids meet, also referred to as the medial canthus) may be used for temperature detection. In particular, the inner canthus may be used as a general approximation of body temperature. As such, an elevated inner canthus temperature may be associated with an overall elevated body temperature.

However, conventional approaches to inner canthus temperature detection may be subject to error. For example, the inner canthus may comprise a relatively small portion of an overall thermal image captured of a human face or body. Accordingly, the inner canthus may be associated with only a small number of pixels of a captured thermal image. As a result, the measured temperature value associated with the inner canthus may decrease significantly with distance due to the influence of other stray thermal wavelengths from other neighboring facial features. The inner canthus may also be difficult to detect, especially when a person is wearing a mask or other face covering.

Accordingly, there is a need for an improved approach to temperature detection using thermal imaging of the inner canthus that provides improved accuracy over conventional techniques.

SUMMARY

Various techniques are disclosed to provide for improved human body temperature detection using thermal images of an inner canthus. In particular, thermal imaging systems and related methods are provided in which distance-related temperature attenuation is compensated to improve the accuracy of human body temperature detection. Such techniques can be particularly useful in the accurate detection of possible elevated human body temperature associated with possible health conditions.

Various techniques are disclosed to provide for improved face detection. For example, thermal imaging systems and related methods are provided in which a face and an inner canthus of a human being in a thermal image are detected, and a temperature measurement of the inner canthus and a body temperature of the human being are determined. An alarm may be triggered and/or a notification may be generated based on the determined temperature(s), such as to identify an elevated body temperature exceeding a threshold (e.g., exceeding a running average of a statistical model of temperature measurements).

In one embodiment, a method includes capturing a thermal image of a human being using a thermal imager; determining a correction term as a function of a distance between the thermal imager and the human being; and applying the correction term to provide a corrected temperature measurement associated with an inner canthus of a face of the human being to compensate for attenuation associated with the distance.

In another embodiment, a system includes a thermal imager; and a logic device configured to: operate the thermal imager to capture a thermal image of a human being, determine a correction term as a function of a distance between the thermal imager and the human being, and apply the correction term to provide a corrected temperature measurement associated with an inner canthus of a face of the human being to compensate for attenuation associated with the distance.

In another embodiment, a method includes capturing a thermal image of a human being using a thermal imager, detecting a face and an inner canthus of the human being in the thermal image using an artificial neural network, determining a temperature measurement of the inner canthus using corresponding pixels of the thermal image, and determining a body temperature of the human being using the temperature measurement.

In another embodiment, a system includes a thermal imager and a logic device configured to: operate the thermal imager to capture a thermal image of a human being, detect a face and an inner canthus of the human being in the thermal image using an artificial neural network, determine a temperature measurement of the inner canthus using corresponding pixels of the thermal image, and determine a body temperature of the human being using the temperature measurement.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 13-18 illustrate various overlays used to provide feedback to a user regarding temperature calculation and a determined temperature measurement in accordance with one or more embodiments of the disclosure.

Embodiments of the present invention and their advantages are best understood by referring to the detailed description that follows. It should be appreciated that like reference numerals are used to identify like elements illustrated in one or more of the figures.

DETAILED DESCRIPTION

Figure 1:
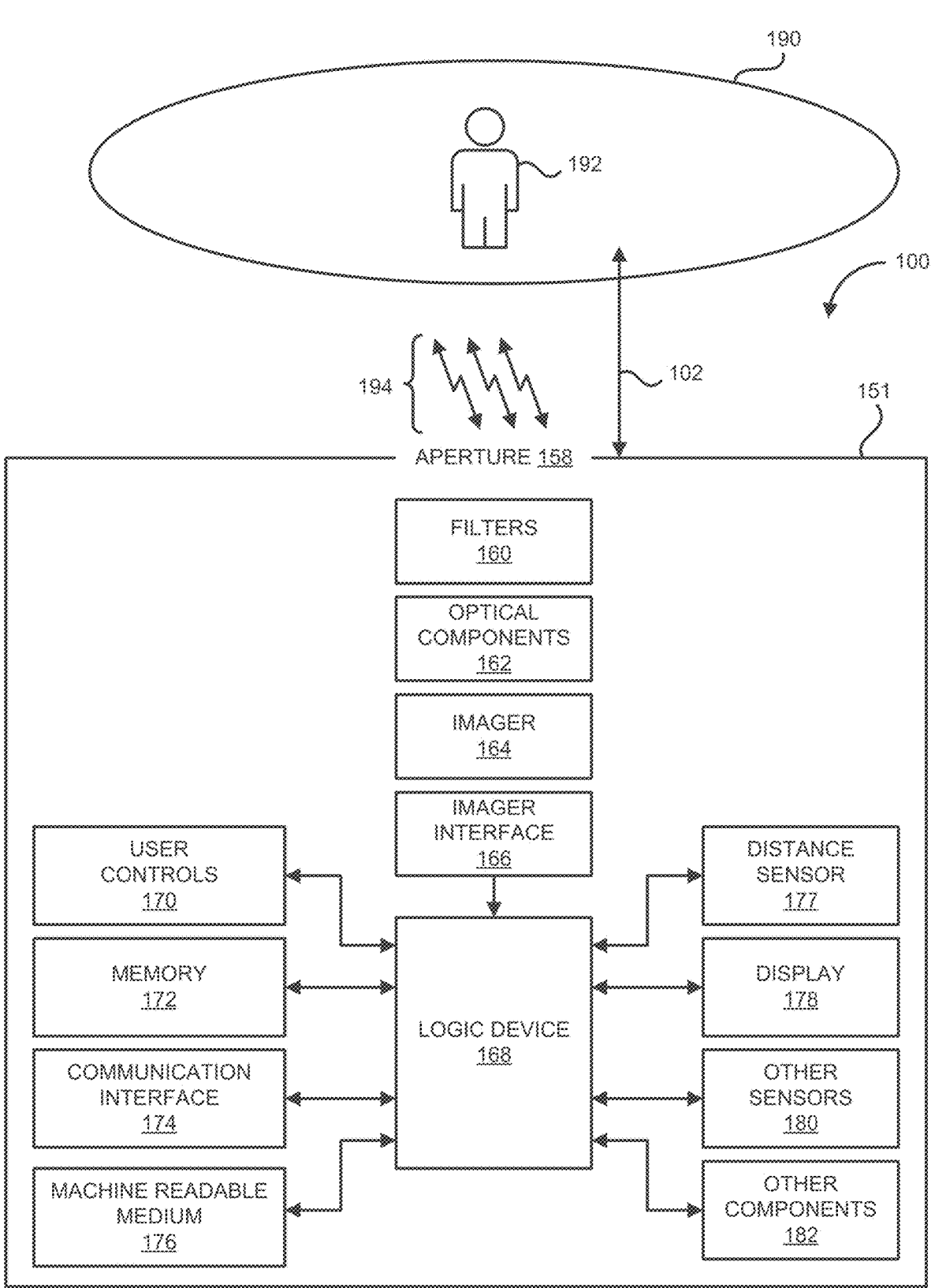
FIG. 1 illustrates a block diagram of an imaging system in accordance with an embodiment of the disclosure.

In accordance with embodiments further discussed herein, various methods and systems are provided in which thermal images are processed to determine temperatures of human beings (e.g., persons) in a manner that compensates for possible distance attenuation. In particular, the techniques discussed herein are particularly useful for providing accurate temperature measurements of the inner canthus of a human being.

In this regard, the inner canthus is often the warmest feature on the face of a human being and is a reasonable approximation of body temperature (e.g., elevated temperatures of the inner canthus may be associated with elevated core body temperatures generally). Thus, by improving the accuracy of inner canthus temperature measurements, the elevated body temperatures associated with various health conditions may be more accurately detected.

When a thermal image is captured of a human being's face, most of the thermal radiation associated with the inner canthus is provided by a small number of pixels of the resulting thermal image. However, those pixels and other surrounding pixels may also be associated with thermal radiation contributions from other portions of the face (e.g., eyes, eyebrows, nose, etc.). This effect can become more pronounced as distance is increased. For example, at greater distances, a smaller number of pixels (e.g., and therefore a smaller proportion of the overall pixels of the thermal image) will be associated with the inner canthus itself, and an increasingly greater number (e.g., larger proportion) of pixels will be associated with other portions of the face. As a result, the overall influence thermal radiation associated with the inner canthus will be reduced in captured thermal images as the distance to the human being increases. Accordingly, when such thermal images are processed to detect the temperature of the inner canthus (e.g., and thus used to detect a possible elevated body temperature), the detected temperature may vary greatly with distance. Such distance-based temperature variations may create difficulties in accurately detecting possible elevated body temperature.

In accordance with embodiments discussed herein, compensation techniques are provided in which correction terms may be applied to the temperature measurements associated with the inner canthus of a human being that are detected using thermal images. For example, the facial width and/or facial area (e.g., in pixels) of a human being in the thermal images may be used to determine correction terms which may be applied to the detected temperatures to provide compensated temperatures. By applying the correction terms, the resulting compensated temperatures can provide a stable representation of the inner canthus temperature, regardless of the distance between the thermal imager and the imaged human being.

Such implementations are particularly useful for applications where there is a need to measure temperatures of multiple human beings at different distances, such as in the case of scanning crowds of people for possible elevated temperatures. By applying correction terms as discussed herein, accurate body temperatures may be determined in such applications, even when people are distributed at different distances from a thermal imaging system.

Also in accordance with embodiments discussed herein, various techniques are included to provide user feedback regarding temperatures, position relative to a thermal imager, and other features. In some embodiments, a statistical analysis may be used to provide a running average of user body temperatures. Such a running average may be used to determine a threshold to detect elevated body temperatures.

Turning now to the drawings, FIG. 1 illustrates a block diagram of an imaging system 100 in accordance with an embodiment of the disclosure. As shown, imaging system 100 includes a housing 151 (e.g., a camera body) having an aperture 158, one or more filters 160, one or more optical components 162, a thermal imager 164, an imager interface 166, a logic device 168, user controls 170, a memory 172, a communication interface 174, a machine readable medium 176, a distance sensor 177, a display 178, other sensors 180, and other components 182.

In various embodiments, imaging system 100 may be implemented, for example, as a camera system such as a portable (e.g., handheld) thermal camera system, a small form factor camera system implemented as part of another device, a fixed camera system, and/or other appropriate implementations. Imaging system 100 may be positioned to receive infrared radiation 194 from a scene 190 (e.g., a field of view of imaging system 100). In various embodiments, scene 190 may include various features of interest such as one or more persons 192 (e.g., human beings).

As shown, a human being 192 (e.g., a person) may be positioned at a distance 102 from imaging system 100. In various embodiments, distance 102 may change over time. For example, if human being 192 and/or imaging system 100 are in motion while a sequence of thermal images are captured, then different thermal images may be captured with different associated distances 102.

Distance sensor 177 may be implemented as any appropriate type of device used to detect distance 102. Such implementations may include, for example, time of flight sensors, LIDAR systems, radar systems, and/or others as appropriate. In some embodiments, distance 102 may be determined using other techniques such as processing thermal images to determine the number of pixels in the thermal images associated with various features of human being 192 as also discussed herein.

Infrared radiation 194 is received through aperture 158 and passes through one or more filters 160 which may be provided to selectively filter particular thermal wavelengths of interest for images to be captured by thermal imager 164. Optical components 162 (e.g., an optical assembly including one or more lenses, additional filters, transmissive windows, and/or other optical components) pass the filtered infrared radiation 194 for capture by thermal imager 164.

Thus, it will be appreciated that filters 160 and/or optical components 162 may operate together to selectively filter out portions of infrared radiation 194 such that only desired wavelengths and/or desired thermal radiation intensities are ultimately received by thermal imager 164. In various embodiments, any desired combination of such components may be provided (e.g., various components may be included and/or omitted as appropriate for various implementations).

Thermal imager 164 may capture thermal images of scene 190 in response to infrared radiation 194. Thermal imager 164 may include an array of sensors for capturing thermal images (e.g., thermal image frames) of scene 190. In some embodiments, thermal imager 164 may also include one or more analog-to-digital converters for converting analog signals captured by the sensors into digital data (e.g., pixel values) to provide the captured images. Imager interface 166 provides the captured images to logic device 168 which may be used to process the images, store the original and/or processed images in memory 172, and/or retrieve stored images from memory 172. Additional implementation details of an embodiment of thermal imager 164 are further discussed herein with regard to FIG. 2.

Logic device 168 may include, for example, a microprocessor, a single-core processor, a multi-core processor, a microcontroller, a programmable logic device configured to perform processing operations, a digital signal processing (DSP) device, one or more memories for storing executable instructions (e.g., software, firmware, or other instructions), and/or any other appropriate combinations of devices and/or memory to perform any of the various operations described herein. Logic device 168 is configured to interface and communicate with the various components of imaging system 100 to perform various method and processing steps described herein. In various embodiments, processing instructions may be integrated in software and/or hardware as part of logic device 168, or code (e.g., software and/or configuration data) which may be stored in memory 172 and/or a machine readable medium 176. In various embodiments, the instructions stored in memory 172 and/or machine readable medium 176 permit logic device 168 to perform the various operations discussed herein and/or control various components of system 100 for such operations.

Memory 172 may include one or more memory devices (e.g., one or more memories) to store data and information. The one or more memory devices may include various types of memory including volatile and non-volatile memory devices, such as RAM (Random Access Memory), ROM (Read-Only Memory), EEPROM (Electrically-Erasable Read-Only Memory), flash memory, fixed memory, removable memory, and/or other types of memory.

Machine readable medium 176 (e.g., a memory, a hard drive, a compact disk, a digital video disk, or a flash memory) may be a non-transitory machine readable medium storing instructions for execution by logic device 168. In various embodiments, machine readable medium 176 may be included as part of imaging system 100 and/or separate from imaging system 100, with stored instructions provided to imaging system 100 by coupling the machine readable medium 176 to imaging system 100 and/or by imaging system 100 downloading (e.g., via a wired or wireless link) the instructions from the machine readable medium (e.g., containing the non-transitory information).

Logic device 168 may be configured to process captured images and provide them to display 178 for presentation to and viewing by the user. Display 178 may include a display device such as a liquid crystal display (LCD), an organic light-emitting diode (OLED) display, and/or other types of displays as appropriate to display images and/or information to the user of system 100. Logic device 168 may be configured to display images and information on display 178. For example, logic device 168 may be configured to retrieve images and information from memory 172 and provide images and information to display 178 for presentation to the user of system 100. Display 178 may include display electronics, which may be utilized by logic device 168 to display such images and information.

User controls 170 may include any desired type of user input and/or interface device having one or more user actuated components, such as one or more buttons, slide bars, knobs, keyboards, joysticks, and/or other types of controls that are configured to generate one or more user actuated input control signals. In some embodiments, user controls 170 may be integrated with display 178 as a touchscreen to operate as both user controls 170 and display 178. Logic device 168 may be configured to sense control input signals from user controls 170 and respond to sensed control input signals received therefrom. In some embodiments, portions of display 178 and/or user controls 170 may be implemented by appropriate portions of a tablet, a laptop computer, a desktop computer, and/or other types of devices.

In various embodiments, user controls 170 may be configured to include one or more other user-activated mechanisms to provide various other control operations of imaging system 100, such as auto-focus, menu enable and selection, field of view (FoV), brightness, contrast, gain, offset, spatial, temporal, and/or various other features and/or parameters.

Imaging system 100 may include various types of other sensors 180 including, for example, microphones, navigation sensors, temperature sensors, and/or other sensors as appropriate.

Logic device 168 may be configured to receive and pass images from imager interface 166 and signals and data from motion sensor 177, sensors 180, and/or user controls 170 to one or more external devices (e.g., remote systems) through communication interface 174 (e.g., through wired and/or wireless communications). In this regard, communication interface 174 may be implemented to provide wired communication over a cable and/or wireless communication over an antenna. For example, communication interface 174 may include one or more wired or wireless communication components, such as an Ethernet connection, a wireless local area network (WLAN) component based on the IEEE 802.11 standards, a wireless broadband component, mobile cellular component, a wireless satellite component, or various other types of wireless communication components including radio frequency (RF), microwave frequency (MWF), and/or infrared frequency (IRF) components configured for communication with a network. As such, communication interface 174 may include an antenna coupled thereto for wireless communication purposes. In other embodiments, the communication interface 174 may be configured to interface with a DSL (e.g., Digital Subscriber Line) modem, a PSTN (Public Switched Telephone Network) modem, an Ethernet device, and/or various other types of wired and/or wireless network communication devices configured for communication with a network.

In some embodiments, a network may be implemented as a single network or a combination of multiple networks. For example, in various embodiments, the network may include the Internet and/or one or more intranets, landline networks, wireless networks, and/or other appropriate types of communication networks. In another example, the network may include a wireless telecommunications network (e.g., cellular phone network) configured to communicate with other communication networks, such as the Internet. As such, in various embodiments, imaging system 100 and/or its individual associated components may be associated with a particular network link such as for example a URL (Uniform Resource Locator), an IP (Internet Protocol) address, and/or a mobile phone number.

Imaging system 100 may include various other components 182 such as speakers, additional displays, visual indicators (e.g., recording indicators), vibration actuators, a battery or other power supply (e.g., rechargeable or otherwise), and/or additional components as appropriate for particular implementations.

Although various features of imaging system 100 are illustrated together in FIG. 1, any of the various illustrated components and subcomponents may be implemented in a distributed manner and used remotely from each other as appropriate.

Although imaging system 100 has been described in the context of a thermal imaging system, other embodiments are also contemplated. In some embodiments, aperture 158, filters 160, optical components 162, and/or imager 164 may be implemented to pass and capture other wavelengths such as visible light wavelengths in addition to or instead of thermal wavelengths. For example, imaging system 100 may be implemented to capture both thermal images and visible light images of scene 190 for comparison with each other to detect scaling or other phenomena. As another example, different imaging systems 100 implemented for different wavelengths may be used to capture thermal images and visible light images of scene 190.

Figure 2:
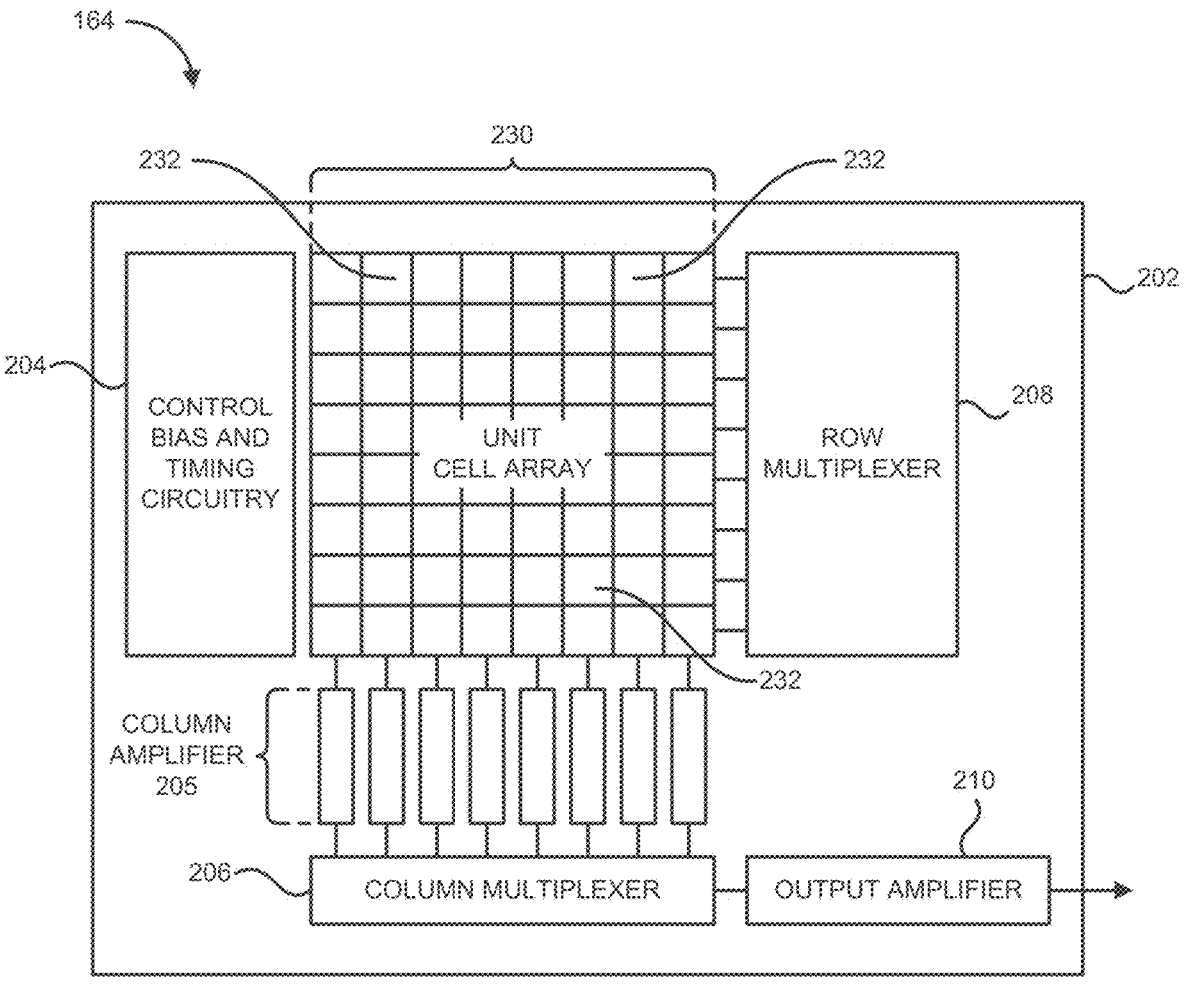
FIG. 2 illustrates a block diagram of a thermal imager in accordance with an embodiment of the disclosure.

FIG. 2 illustrates a block diagram of thermal imager 164 in accordance with an embodiment of the disclosure. In this illustrated embodiment, thermal imager 164 is a focal plane array (FPA) including a sensor array 230 of infrared sensors 232 (e.g., implemented as unit cells) and a read out integrated circuit (ROIC) 202. Although an 8 by 8 array of infrared sensors 232 is shown (e.g., corresponding to rows and columns of pixels), this is merely for purposes of example and ease of illustration. Any desired sensor array size may be used as desired.

Each infrared sensor 232 may be implemented, for example, by an infrared detector such as a microbolometer and associated circuitry to provide image data (e.g., a data value associated with a captured voltage) for a pixel of a captured thermal image. In this regard, time-multiplexed electrical signals may be provided by the infrared sensors 232 to ROIC 202.

ROIC 202 includes bias generation and timing control circuitry 204, column amplifiers 205, a column multiplexer 206, a row multiplexer 208, and an output amplifier 210. Images captured by infrared sensors 232 may be provided by output amplifier 210 to logic device 168 and/or any other appropriate components to perform various processing techniques described herein. Further descriptions of ROICs and infrared sensors (e.g., microbolometer circuits) may be found in U.S. Pat. No. 6,028,309 issued Feb. 22, 2000, which is incorporated herein by reference in its entirety.

Figure 3:
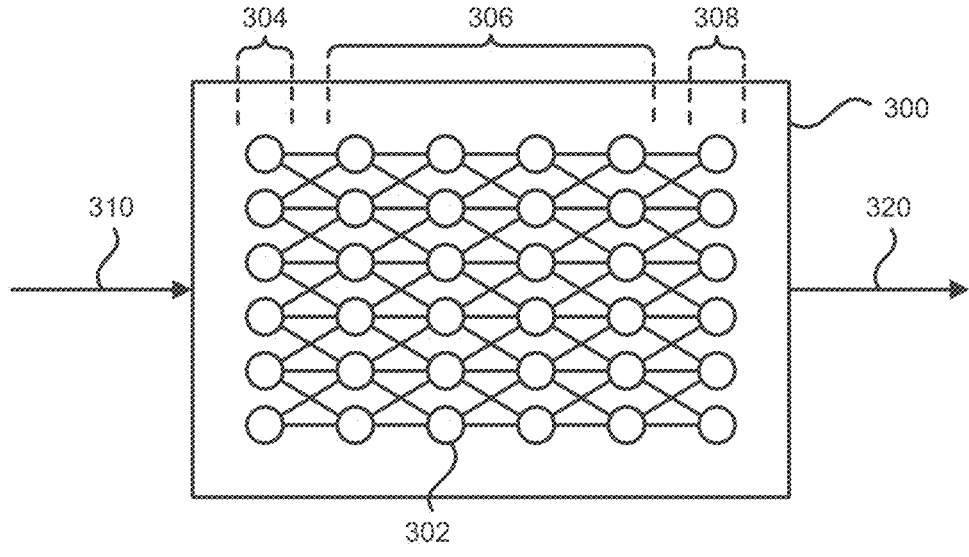
FIG. 3 illustrates a block diagram of an artificial neural network in accordance with an embodiment of the disclosure.

FIG. 3 illustrates a block diagram of an artificial neural network 300 in accordance with an embodiment of the disclosure. For example, in some embodiments, neural network 300 may be implemented by logic device 168.

As shown, neural network 300 includes various nodes 302 arranged in multiple layers including an input layer 304 receiving one or more inputs 310, hidden layers 306, and an output layer 308 providing one or more outputs 320. Although particular numbers of nodes 302 and layers 304, 306, and 308 are shown, any desired number of such features may be provided in various embodiments.

In some embodiments, neural network 300 may be used to perform face detection on various thermal images captured by imaging system 100 and provided to inputs 310 of neural network 300. The results of such face detection may be provided by neural network at outputs 320. In some embodiments, neural network 300 may be trained by providing thermal images of human faces (e.g., stored in machine readable medium 176) to inputs 310.

Figure 4:
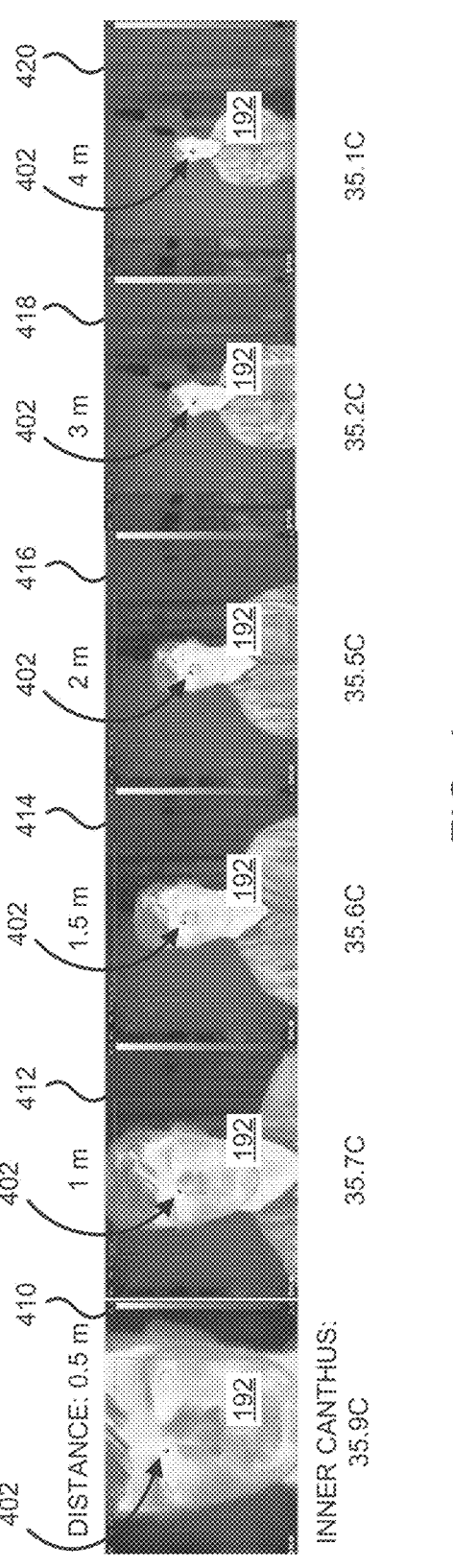
FIG. 4 illustrates a sequence of thermal images captured at different distances in accordance with an embodiment of the disclosure.

FIG. 4 illustrates a sequence of thermal images 410 to 420 captured of human being 192 at different distances in accordance with an embodiment of the disclosure. For example, as shown, thermal images 410 to 420 have been captured at various distances ranging from 0.5 meters to 4 meters. As also shown, an inner canthus 402 of the human being 192 is present in each of the thermal images 410 to 420. However, the size of the inner canthus 402 becomes increasingly smaller in thermal images 410 to 420 as the distance increases. In this regard, the number of pixels in thermal images 410 to 420 associated with the inner canthus 402 are also correspondingly reduced as the distance increases. Moreover, the contributions of other facial features will become proportionally higher, thus causing the overall temperature of the captured pixels associated with the inner canthus 402 to decrease.

For example, as further shown in FIG. 4, the detected uncompensated temperature of the inner canthus 402 (e.g., performed by processing the values of the pixels determined to be associated with the inner canthus 402) decreases with distance from a high of 35.9 degrees C. at a distance of 0.5 meters to a low of 35.1 degrees C. at a distance of 4 meters (e.g., a change of 0.8 degrees C.). This change can be significant in the context of elevated body temperature detection, as such an error may determine whether a human being's measured body temperature crosses a threshold associated with a health condition.

In accordance with various embodiments discussed herein, correction terms may be determined to compensate for such distance-based attenuation. In this regard, the correction terms may be functions of distance. For example, this can be generally represented by the following equation 1:

$$CompensatedTemp = MeasuredTemp + \text{Correction}(Distance) \qquad \text{(eq. 1)}$$

In equation 1, CompensatedTemp is the corrected temperature measurement (e.g., compensated temperature value) of inner canthus 402 compensated for distance, MeasuredTemp is the uncompensated temperature measurement of inner canthus 402 determined by analyzing a thermal image, and Correction is a correction term applied to the MeasuredTemp as a function of Distance, where Distance is distance 102 from imaging system 100 and human being 192. Accordingly, Correction(Distance) as set forth in equation 1 may use an appropriate distance-based correlation to provide a correction term in various embodiments.

Distance 102 may be determined through various techniques. For example, in some embodiments, distance 102 may be determined by distance sensor 177 using appropriate types of sensors and/or systems as discussed. In some embodiments, distance 102 may be determined by referencing other possible features in scene 190 that have known distances to imaging system 100.

Figure 5:
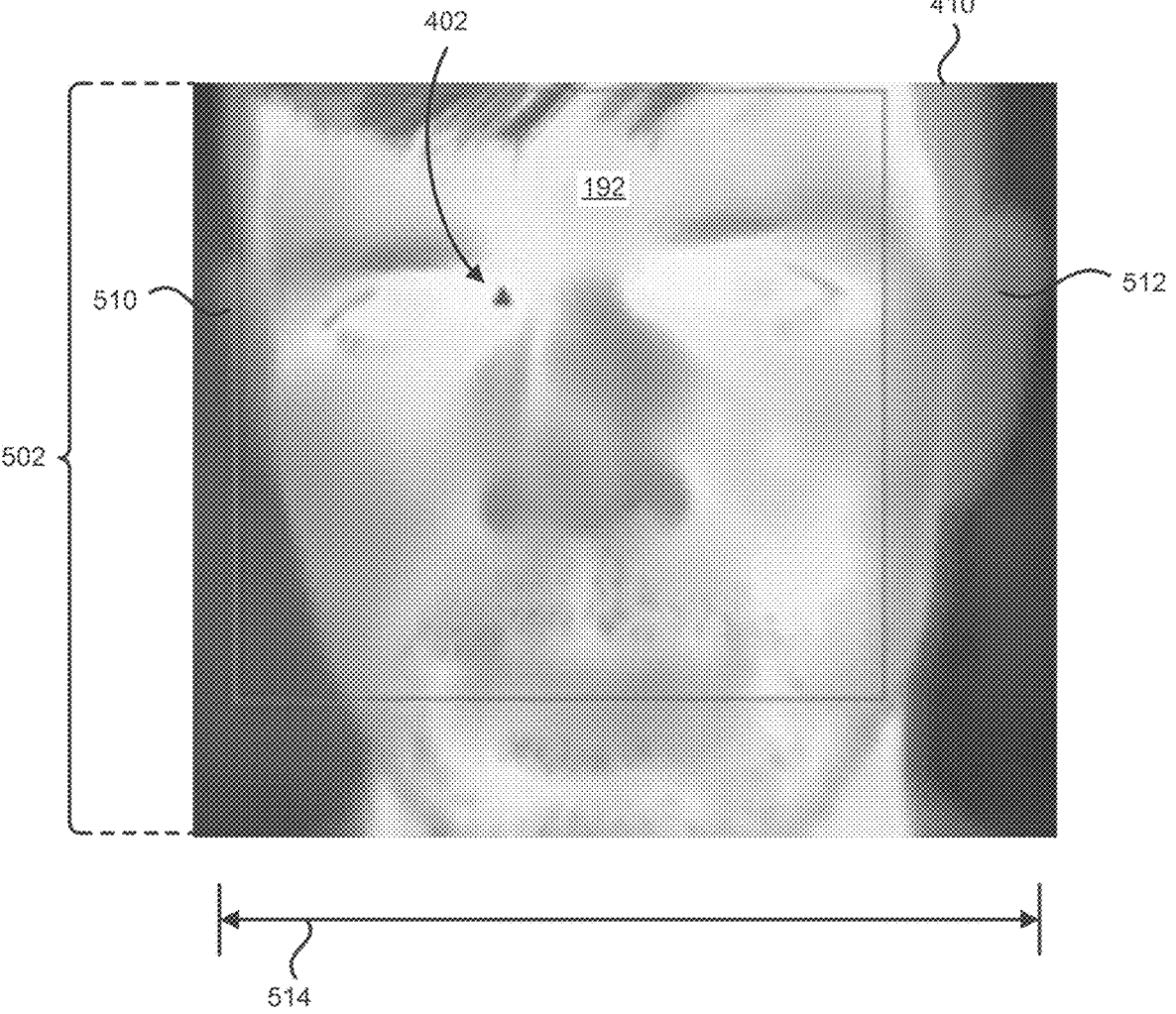
FIG. 5 illustrates a thermal image undergoing a distance analysis in accordance with an embodiment of the disclosure.

In some embodiments, distance 102 may be determined by performing an analysis of one or more captured thermal images of human being 192. For example, FIG. 5 illustrates thermal image 402 undergoing a distance analysis in accordance with an embodiment of the disclosure. In some embodiments, logic device 168 may perform the analysis discussed in relation to FIG. 5.

In FIG. 5, thermal image 402 is processed to detect a face 502 of human being 192 including ears 510 and 512. In addition, a face width (e.g., also referred to as "ear2ear" or "e2e") 514 between ears 510 and 512 is calculated. This face width 514 can be used to determine an approximate distance 102. In this regard, imaging system 100 may be precalibrated (e.g., with appropriate information stored in machine readable medium 176) to correlate face width 514 (e.g., number of pixels across width 514) with distance 102. For example, human beings generally have face widths in a relatively narrow range (e.g., generally 12 cm to 16 cm). As a result, imaging system 100 may store a predetermined correlation between the number of pixels associated with a detected face (e.g., face width 514 being assumed to be an average face width) and distance 102. Thus, by determining the number of pixels of thermal image 410 associated with face width 514, imaging system 100 may determine an approximate value for distance 102.

Although a correlation between face width 514 and distance 102 has been discussed, other correlations may also be used, such as determining the number of pixels associated with the area of face 502 (e.g., number of pixels of the thermal image associated with the face) and precalibrating imaging system 100 to correlate average face area with distance 102.

Considering the face width 514 correlation in more detail, equation 1 can be updated to specifically address face width 514 (e.g., "ear2ear" or "e2e") as set forth in the following equation 2:

$$CompensatedTemp = MeasuredTemp + \text{Correction(ear2ear)} \qquad \text{(eq. 2)}$$

In equation 2, ear2ear is the number of pixels in thermal image 410 associated with face width 514. In some embodiments, the correction term Correction(ear2ear) may be determined in accordance with the following equation 3:

$$\text{Correction(ear2ear)} = p1/(p2 + \text{ear2ear}) \qquad \text{(eq. 3)}$$

In equation 3, p1 and p2 are fitting constants corresponding to the predetermined correlation between face width 514 (e.g., ear2ear) and distance 102.

Upon review of equation 3, it will be appreciated that as the ear2ear value decreases (e.g., corresponding to face width 514 decreasing which is associated with greater values of distance 102), the magnitude of Correction(ear2ear) (e.g., the correction term) increases to compensate for distance-based attenuation for pixels associated with inner canthus 402.

Figure 6:
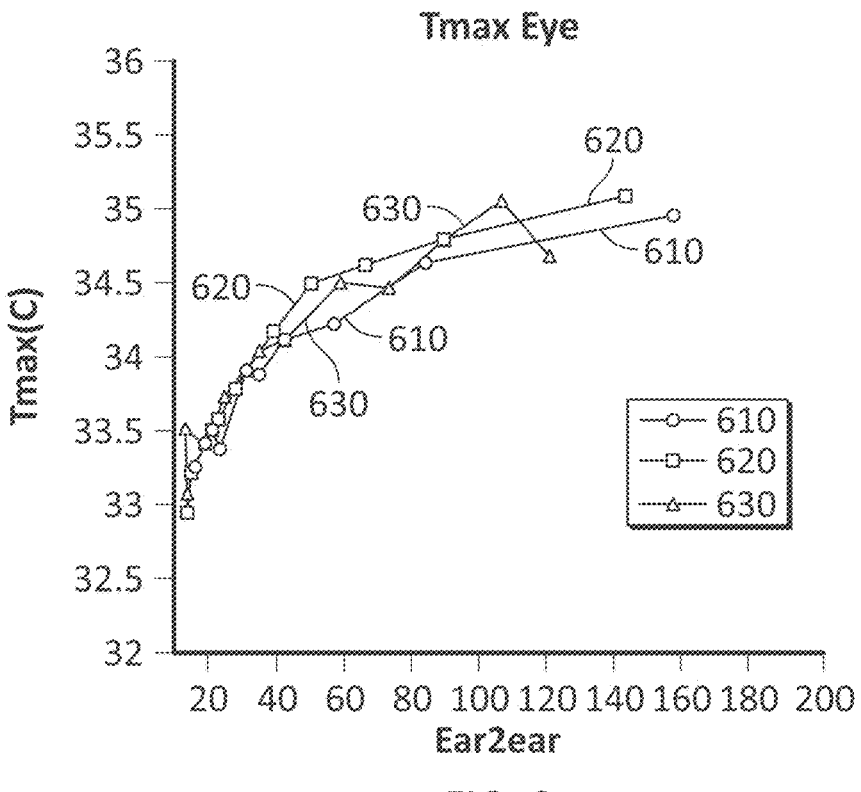
FIG. 6 illustrates plots of uncompensated temperature measurements in accordance with an embodiment of the disclosure.
Figure 7:
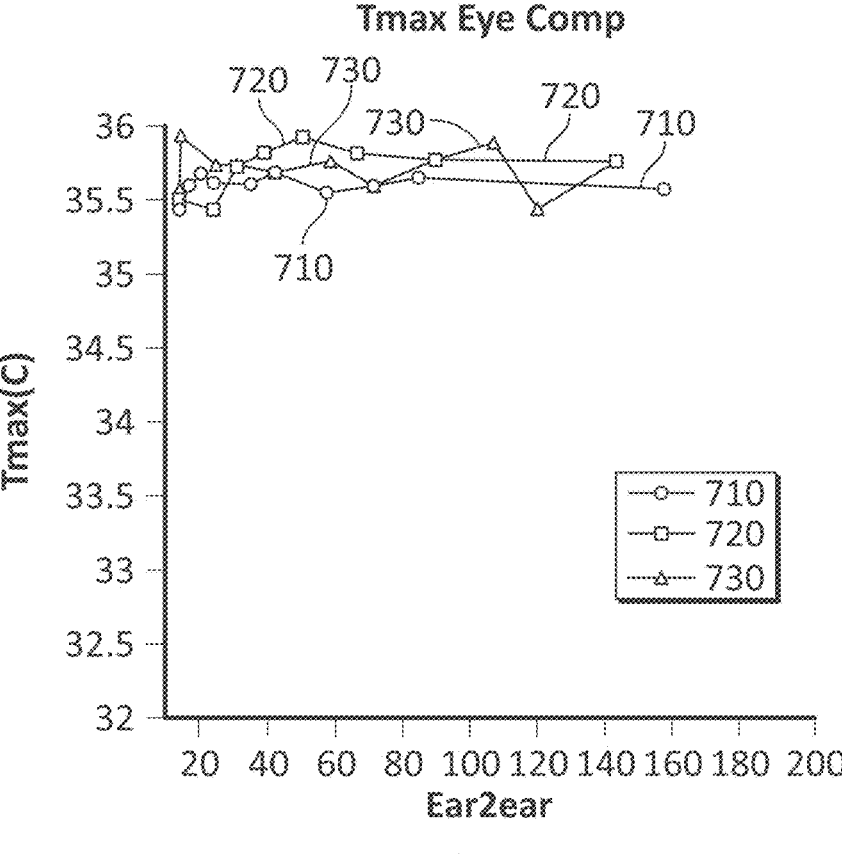
FIG. 7 illustrates plots of corrected temperature measurements in accordance with an embodiment of the disclosure.

The results of this compensation can be further appreciated upon review of FIGS. 6 and 7. In this regard, FIG. 6 illustrates plots 610, 620, and 630 of uncompensated temperature measurements in accordance with an embodiment of the disclosure. In particular, plots 610, 620, and 630 illustrate uncompensated temperature measurements determined for the inner canthus 402 (denoted Tmax(C) along the vertical axis) and the corresponding face width 514 (denoted ear2ear along the horizontal axis) of three different human beings 192 determined from a sequence of thermal images (e.g., each of plots 610, 620, and 630 correspond to temperature measurements associated with a different human being 192). It will be appreciated that larger values of ear2ear correspond to smaller distances 102 associated with the captured thermal images. As shown, plots 610, 620, and 630 demonstrate a substantial distance-based attenuation in temperature measurements of approximately 2 degrees C. (e.g., ranging from a low of approximately 32.9 degrees C. to a high of approximately 35 degrees C.

In contrast, FIG. 7 illustrates plots 710, 720, and 730 of corrected temperature measurements in accordance with an embodiment of the disclosure. In particular, plots 710, 720, and 730 illustrate corrected (e.g., distance-compensated) temperature measurements determined for the inner canthus 402 and the corresponding face width 514 using the same thermal images of FIG. 6. For example, in some embodiments, the corrected temperature measurements of FIG. 7 may be determined by applying appropriate correction terms (e.g., in accordance with the techniques discussed with regard to equations 1 to 3) to the uncompensated temperature measurements of FIG. 6.

As shown, plots 710, 720, and 730 demonstrate substantially uniform temperature measurements for each human being 192 within a small temperature range (e.g., ranging from a low of approximately 35.4 degrees C. to a high of approximately 36 degrees C.). Moreover, the variation in plot 710 is particularly well contained in a range of only 0.1 degrees C. Comparing the compensated temperature measurements of plots 710, 720, and 730 with the uncompensated temperature measurements of plots 610, 620, and 630, it is clear that the compensated temperature measurements provide a reliable representation of canthus temperature, independent of distance 102.

Figure 8:
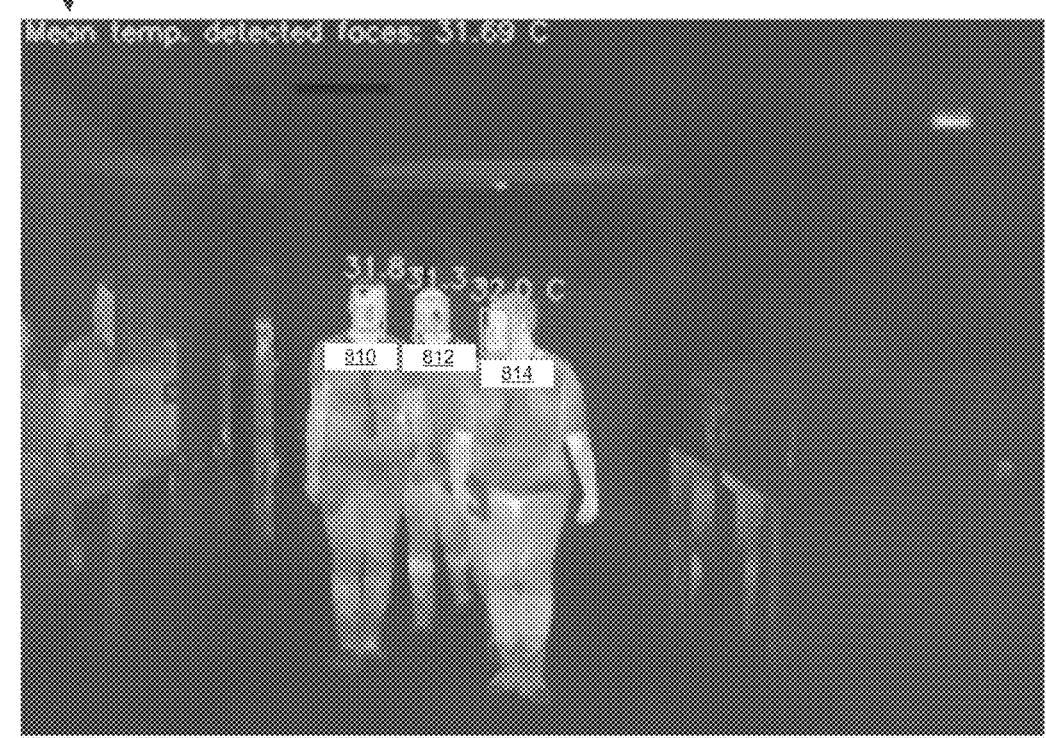
FIGS. 8 and 9 illustrate thermal images with associated uncompensated temperature measurements in accordance with embodiments of the disclosure.
Figure 9:
Figure 10:
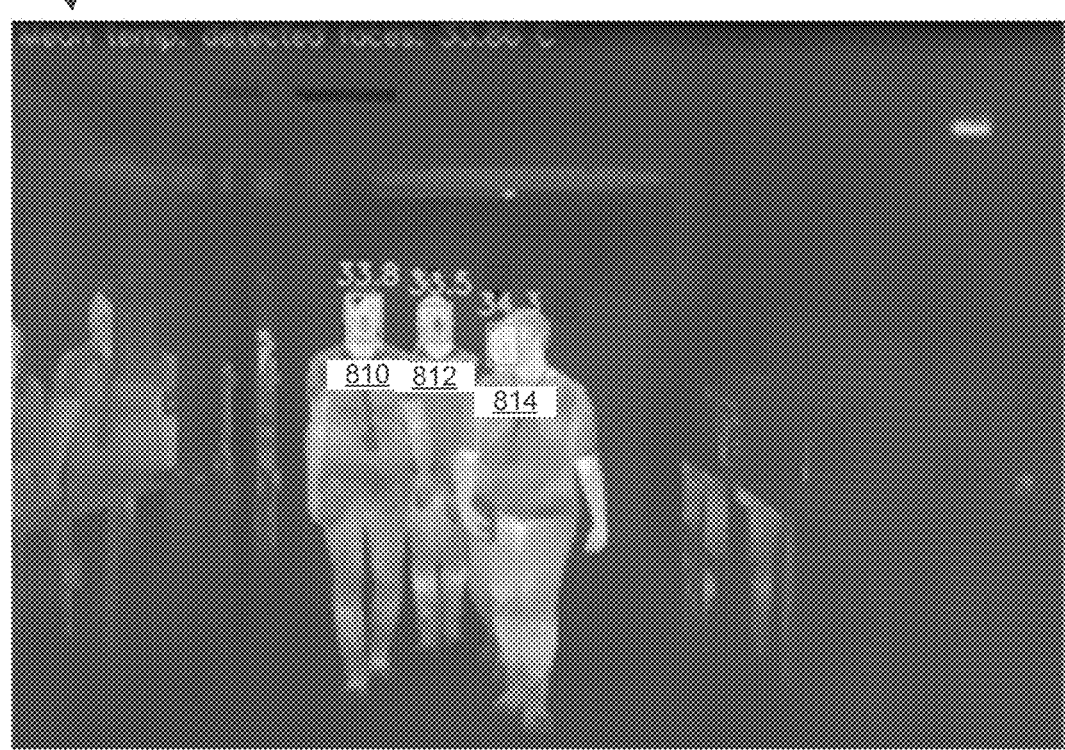
FIGS. 10 and 11 illustrate thermal images with associated corrected temperature measurements in accordance with embodiments of the disclosure.

FIGS. 8 to 10 further illustrate the results of the temperature compensation techniques discussed herein. For example, FIGS. 8 and 9 illustrate thermal images 800 and 900 with associated uncompensated temperature measurements in accordance with embodiments of the disclosure. In FIG. 8, thermal image 800 has been captured at a far distance (e.g., approximately 20 feet) from thermal imaging system 100. The detected canthus temperatures of human beings 810, 812, and 814 are 31.8 degrees C., 31.3 degrees C., and 32.0 degrees C., respectively. In addition, the mean temperature for all human beings is 31.69 degrees C.

In FIG. 9, thermal image 900 has been captured at a close distance (e.g., approximately 5 feet) from thermal imaging system 100. The detected canthus temperatures of human beings 810, 812, and 814 are 33.2 degrees C., 32.5 degrees C., and 33.1 degrees C., respectively (e.g., all higher than those of FIG. 8). In addition, the mean temperature for all human beings is 32.93 degrees C. (e.g., higher than that of FIG. 8). Accordingly, it will be appreciated that the uncompensated temperature measurements associated with FIGS. 8 and 9 demonstrate significant distance-based attenuation.

Figure 11:
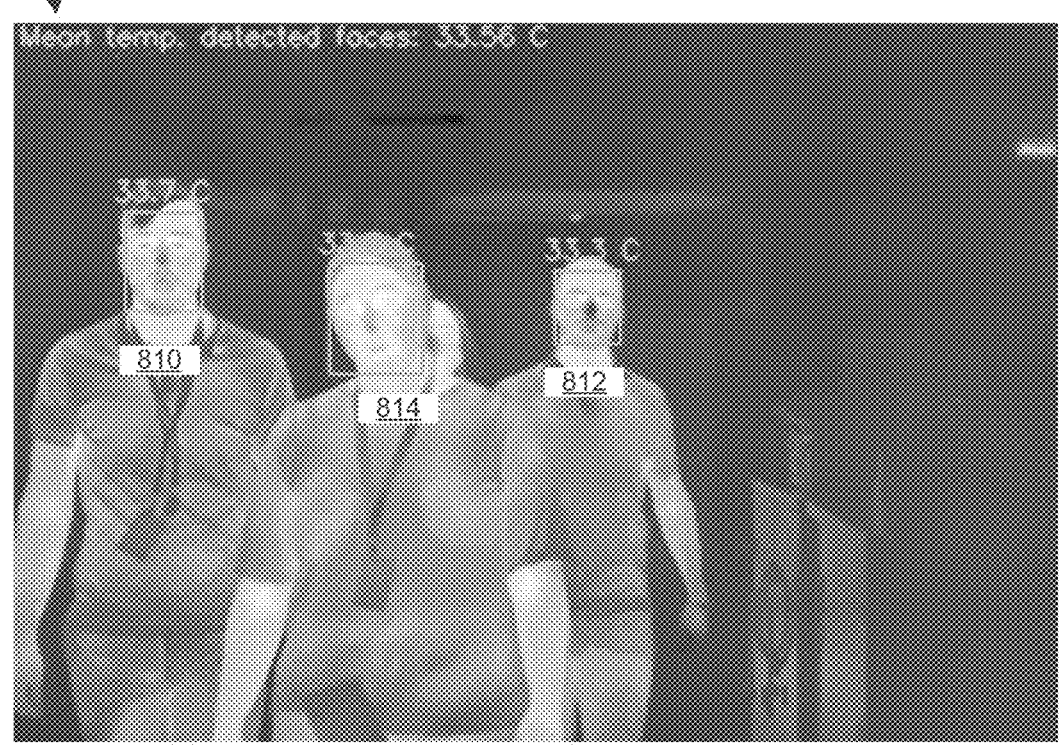

FIGS. 10 and 11 illustrate thermal images 1000 and 1100 with associated compensated temperature measurements in accordance with embodiments of the disclosure. In this regard, thermal images 1000 and 1100 use the same original captured thermal image data as thermal images 800 and 900, but include the results of compensated temperature measurements.

As shown in FIG. 10 (e.g., thermal image 1000 captured at a far distance of approximately 20 feet), the detected canthus temperatures of human beings 810, 812, and 814 are 33.8 degrees C., 33.5 degrees C., and 34.3 degrees C., respectively. In addition, the mean temperature for all human beings is 33.86 degrees C.

In FIG. 11, (e.g., thermal image 1100 captured at a close distance of approximately 5 feet), the detected canthus temperatures of human beings 810, 812, and 814 are 33.7 degrees C., 33.3 degrees C., and 33.6 degrees C., respectively (e.g., all close in temperature to those of FIG. 10). In addition, the mean temperature for all human beings is 33.56 degrees C. (e.g., close in temperature to that of FIG. 10). Accordingly, it will be appreciated that the compensated temperature measurements associated with FIGS. 10 and 11 demonstrate a consistency independent of distance-based attenuation.

Figure 12:
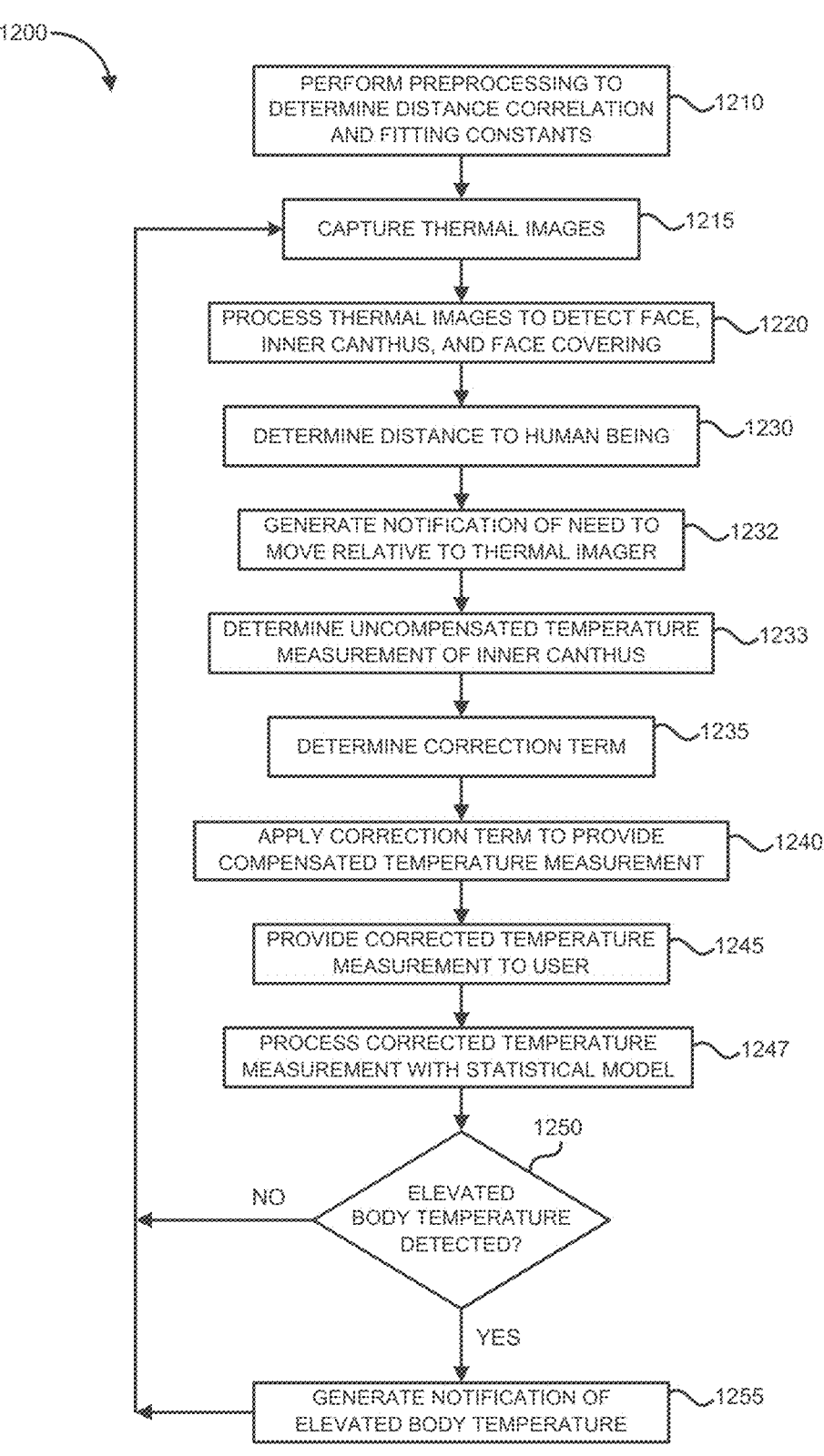
FIG. 12 illustrates a process of determining corrected temperature measurements in accordance with an embodiment of the disclosure.

FIG. 12 illustrates a process 1200 of determining compensated temperature measurements in accordance with an embodiment of the disclosure. In block 1210, logic device 168 performs preprocessing operations (e.g., precalibration) to determine correlations between distance 102 and various features of captured thermal images to determine the fitting constants p1 and p2 of equation 3. For example, in some embodiments, block 1210 may include capturing a plurality of thermal images of objects or human beings at different distances 102 from imaging system 100 to determine correlations between the number of pixels associated with various features (e.g., face width 514 or other human facial features) and different distances 102. Logic device 168 may then determine the value of fitting constants p1 and p2 as appropriate to compensate for distance-related changes in the features captured in thermal images.

In block 1215, thermal imager 164 captures one or more thermal images of one or more human beings 192 of interest in scene 190. For example, thermal imager 164 may be operated by a logic device (e.g., logic device 168) to capture thermal images.

In block 1220, logic device 168 performs face detection (e.g., using neural network 300 and/or other appropriate face detection techniques) to detect the face and the location of the inner canthus 402 of the human being 192 in the captured thermal images. For example, an artificial neural network (e.g., neural network 300), a detection system (e.g., as described below with reference to FIG. 19), and/or other appropriate face detection techniques may be employed by logic device 168 to detect the face and inner canthus 402 of human being 192 in the thermal image. In embodiments, block 1220 may include detecting a face covering, such as a mask or another type of face covering, worn by human being 192 in the captured thermal images.

In block 1230, logic device 168 determines distance 102 to human being 192. As discussed, various techniques may be used. In some embodiments, a pixel-based approach may be performed by determining the face width 514 (e.g., ear2ear value) and/or other facial feature of the human being 192 and correlating the distance 102 (e.g., through a predetermined correlation provided by block 1210). For example, distance 102 may be determined using a predetermined association between the number of pixels of one or more facial features (e.g., facial width, an area of the face, etc.) and the distance, although other configurations are contemplated. In other embodiments, distance sensor 177 and/or other techniques may be used as appropriate.

In block 1232, a notification may be generated regarding distance 102. For example, imaging system 100 may generate a notification of a determined need for human being 192 to move relative to the thermal imager 164 based on the determined distance. For example, imaging system 100 may generate a notification indicating human being 192 is positioned incorrectly, such as outside a preferred distance range from thermal imager 164. As a result, one or more blocks of FIG. 12 may be repeated until human being 192 is positioned correctly in a preferred distance range. In this way, human being 192 can be properly aligned before temperature measurements are taken in subsequent steps, explained below.

In block 1233, logic device 168 determines an uncompensated temperature measurement of the inner canthus 402. For example, block 1233 may include determining a temperature associated with pixel values of the thermal image corresponding to the inner canthus 402. In various embodiments, such temperature may be determined, for example, by averaging and/or otherwise processing the corresponding pixel values.

In block 1235, logic device 168 determines a correction term to be applied to the previously detected uncompensated temperature measurement. For example, the correction term may be determined as a function of the distance between thermal imager 164 and human being 192. In the case of a pixel-based approach as discussed, the correction term may be determined using equation 3. In other embodiments, any appropriate correction term as a function of distance may be used as discussed with regard to equation 1. In embodiments, the correction term may be determined based on an attenuation associated with a face covering (e.g., a mask), as described below. In this manner, process 1200 may compensate for one or more face coverings worn by human being 192, such as those described below with reference to FIGS. 13-18.

In block 1240, logic device 168 applies the correction term to the uncompensated temperature measurement (previously determined in block 1225) to provide a corrected temperature measurement as discussed with regard to FIGS. 7, 10, and 11. For instance, the correction term may be applied to provide a corrected temperature measurement associated with inner canthus 402 to compensate for attenuation associated with distance 102, a face covering, or other factors, as described herein.

In block 1245, imaging system 100 provides the corrected temperature measurement to a user of imaging system 100. For example, in some embodiments, imaging system 100 may provide the corrected temperature measurement as part of a thermal image presented to the user on display 178 similar to thermal images 1000 and 1100 of FIGS. 10 and 11 or thermal images of FIGS. 13-18. The corrected temperature measurement may correlate to a body temperature of human being 192. For example, a measurement system and/or other appropriate temperature determining techniques may be employed by logic device 168 to determine the body temperature of human being 192 based on the temperature of inner canthus 402, as described herein.

In block 1247, logic device 168 processes the corrected temperature measurement with a statistical model. For example, statistical analysis may be used to provide a running average of corrected temperature measurements (e.g., user body temperatures), such as described with reference to FIG. 19. The running average may be used to determine a threshold to detect elevated body temperatures, as explained below.

In block 1250, logic device 168 determines whether the corrected temperature measurement is associated with an elevated body temperature. For example, the corrected temperature measurement may be used to identify a possible health condition associated with human being 192. An elevated body temperature may be determined based on the corrected temperature measurement exceeding a threshold, such as the running average provided by the statistical model in block 1247. If no elevated body temperature is detected, then the process of FIG. 12 returns to block 1215 where additional thermal images may be captured and subsequently processed as discussed.

If an elevated body temperature is detected in block 1250, then the process of FIG. 12 continues to block 1255 where imaging system 100 may generate a notification regarding the elevated body temperature. For example, in various embodiments, imaging system 100 may generate a visible and/or audible notification in the form of text, icons, colors, flashing lights, sounds, alarms, and/or other types notifications using the various components of imaging system 100 as appropriate. The notification regarding the elevated body temperature may include many configurations, such as those described below with reference to FIGS. 13-18. Thereafter, the process of FIG. 12 returns to block 1215 where additional thermal images may be captured and subsequently processed as discussed.

In some embodiments, operations of FIG. 12 may be performed for a plurality of human beings 192 present in the captured thermal image (e.g., as similarly discussed and illustrated with regard to FIGS. 10 and 11). In some embodiments, operations of FIG. 12 may be repeated to provide updated corrected temperature measurements as one or more human beings 192 move through scene 190 and/or with changing distances 102.

Additional embodiments are also contemplated. For example, although correction terms have been discussed as being determined using a correlation between face size (e.g., width and/or area) and distance, other correlations are also possible. For example, in some embodiments, thermal images of human beings 192 having different face sizes (e.g., corresponding to different head sizes) at the same distance 102 from imaging system 100 may result in different temperature measurements (e.g., due to different sizes of the inner canthus for the different face sizes and thus correspondingly different numbers of pixels associated therewith). Accordingly, in some embodiments, correction terms may be further adjusted and/or correlated as appropriate to further compensate for such differences associated with differently sized faces of human beings 192 at the same distance 102 from imaging system 100.

As discussed with regard to blocks 1232, 1245, and 1255 of FIG. 12, various techniques are contemplated to provide user feedback regarding the corrected temperature measurement of inner canthus 402. In embodiments, a user (e.g., human being 192) may look into thermal imager 164 and receive feedback regarding the position of the user relative to thermal imager 164 and/or the determined body temperature of the user. For instance, the user may see an overlay or other notification in the thermal image providing a visual indication of a status of thermal imager 164, a position of the user (e.g., too close, too far away, etc.), and/or a determined body temperature of the user (e.g., below normal, normal, or elevated).

As discussed with regard to block 1247 of FIG. 12, various embodiments utilize a statistical analysis approach in determining an elevated body temperature of the user. For example, a running average of determined body temperatures may be used to set a threshold to accurately determine whether the user is running a fever. For example, such a running average may account for environmental factors (e.g., ambient temperature or other features) that may otherwise affect the body temperatures of human beings.

FIGS. 13-18 illustrate various notifications or indications used to provide feedback to a user regarding temperature calculation and a determined temperature measurement in accordance with one or more embodiments of the disclosure. For example, as discussed with regard to block 1232 of FIG. 12, logic device 168 may generate a notification regarding distance 102 to human being 192. As discussed with regard to block 1245 of FIG. 12, logic device 168 may generate a notification providing the corrected temperature measurement of human being 192. In addition, as discussed with regard to block 1255 of FIG. 12, logic device 168 may generate a notification of elevated body temperature.

FIG. 13 illustrates a first notification 1300. As shown, the first notification 1300 may be an overlay on the face of human being 192, although other configurations are contemplated, including, for example, one or more notifications or interfaces (e.g., a web interface) provided on display 178. The first notification 1300 may be configured to provide a first indication to the user regarding temperature calculation. For instance, first notification 1300 may indicate that the system is currently calculating the temperature of human being 192, that human being 192 is positioned appropriately (e.g., within a preferred distance range), etc. The first notification 1300 may be a first pattern, type, and/or color, such as a cyan colored overlay, to distinguish over other indications, as provided herein. The first notification 1300 may be generated in block 1232 of FIG. 12.

FIG. 14 illustrates a second notification 1400. Like first notification 1300, second notification 1400 may be an overlay on the face of human being 192, a notification, and/or interface (e.g., a web interface) provided on display 178. The second notification 1400 may be configured to provide a second indication to the user regarding temperature calculation. For instance, second notification 1400 may indicate that the system is in a calibration mode, that human being 192 is positioned too close, etc. The second notification 1400 may be a second pattern, type, and/or color, such as a yellow colored overlay, to distinguish over other indications, as provided herein. The second notification 1400 may be generated in block 1232 of FIG. 12.

FIG. 15 illustrates a third notification 1500, which may be an overlay on the face of human being 192, a notification, and/or interface (e.g., a web interface) provided on display 178. The third notification 1500 may be configured to provide a third indication to the user regarding temperature calculation. For instance, third notification 1500 may indicate that human being 192 is positioned incorrectly, such as outside a preferred distance range. In such embodiments, the third notification 1500 may provide feedback instructing human being 192 to move relative to camera to provide thermal image with enough pixels for canthus radiometric measurement, as provided above. The third notification 1500 may be a third pattern, type, and/or color, such as a purple colored overlay, to distinguish over other indications, as provided herein. The third notification 1500 may be generated in block 1232 of FIG. 12.

FIG. 16 illustrates a fourth notification 1600, which may be an overlay on the face of human being 192, a notification, and/or interface (e.g., a web interface) provided on display 178. The fourth notification 1600 may be configured to provide a fourth indication to the user, such as regarding a determined temperature measurement of human being 192. For instance, fourth notification 1600 may indicate that the detected temperature of human being 192 is below normal, such as below a normal range specific to human being 192 or for human beings in general. The fourth notification 1600 may be a fourth pattern, type, and/or color, such as a blue colored overlay, to distinguish over other indications, as provided herein. The fourth notification 1600 may be generated in block 1245 or block 1255 of FIG. 12.

FIG. 17 illustrates a fifth notification 1700, which may be an overlay on the face of human being 192, a notification, and/or interface (e.g., a web interface) provided on display 178. The fifth notification 1700 may be configured to provide a fifth indication to the user, such as regarding a determined temperature measurement of human being 192. For instance, fifth notification 1700 may indicate that the detected temperature of human being 192 is normal, such as within a normal range specific to human being 192 or for human beings in general. The fifth notification 1700 may be a fifth pattern, type, and/or color, such as a green colored overlay, to distinguish over other indications, as provided herein. The fifth notification 1700 may be generated in block 1245 or block 1255 of FIG. 12.

FIG. 18 illustrates a sixth notification 1800, which may be an overlay on the face of human being 192, a notification, and/or interface (e.g., a web interface) provided on display 178. The sixth notification 1800 may be configured to provide a sixth indication to the user, such as regarding a determined temperature measurement of human being 192. For instance, sixth notification 1800 may indicate that the detected temperature of human being 192 is elevated, such as above a normal range specific to human being 192 or for human beings in general. The sixth notification 1800 may be a sixth pattern, type, and/or color, such as a red colored overlay, to distinguish over other indications, as provided herein. The sixth notification 1800 may be generated in block 1245 or block 1255 of FIG. 12.

Referring to FIGS. 13-18, each notification 1300, 1400, 1500, 1600, 1700, or 1800 may be a rectangular overlay capturing the face of human being 192. Such examples are illustrative only, and the notifications 1300, 1400, 1500, 1600, 1700, 1800 may have other configurations, including, for example, circular, ovular, or polygon configurations. In embodiments, each notification 1300, 1400, 1500, 1600, 1700, or 1800 may capture the inner canthus 402 of human being 192. In embodiments, the notifications 1300, 1400, 1500, 1600, 1700, 1800 may highlight the inner canthus 402.

As shown, imaging system 100 (e.g., neural network 300) may detect or accommodate for one or more masks 1310 (or other face coverings) worn by human being 192. For example, correction terms may be determined to compensate for a face covering attenuation. In this regard, the correction terms may be functions of the type of mask 1310, the color of mask 1310, the material properties of mask 1310, the position of the mask 1310 relative to inner canthus 402, and/or other mask properties, etc. The one or more mask properties may be determined by performing an analysis of one or more captured thermal images of human being 192.

Figure 19:
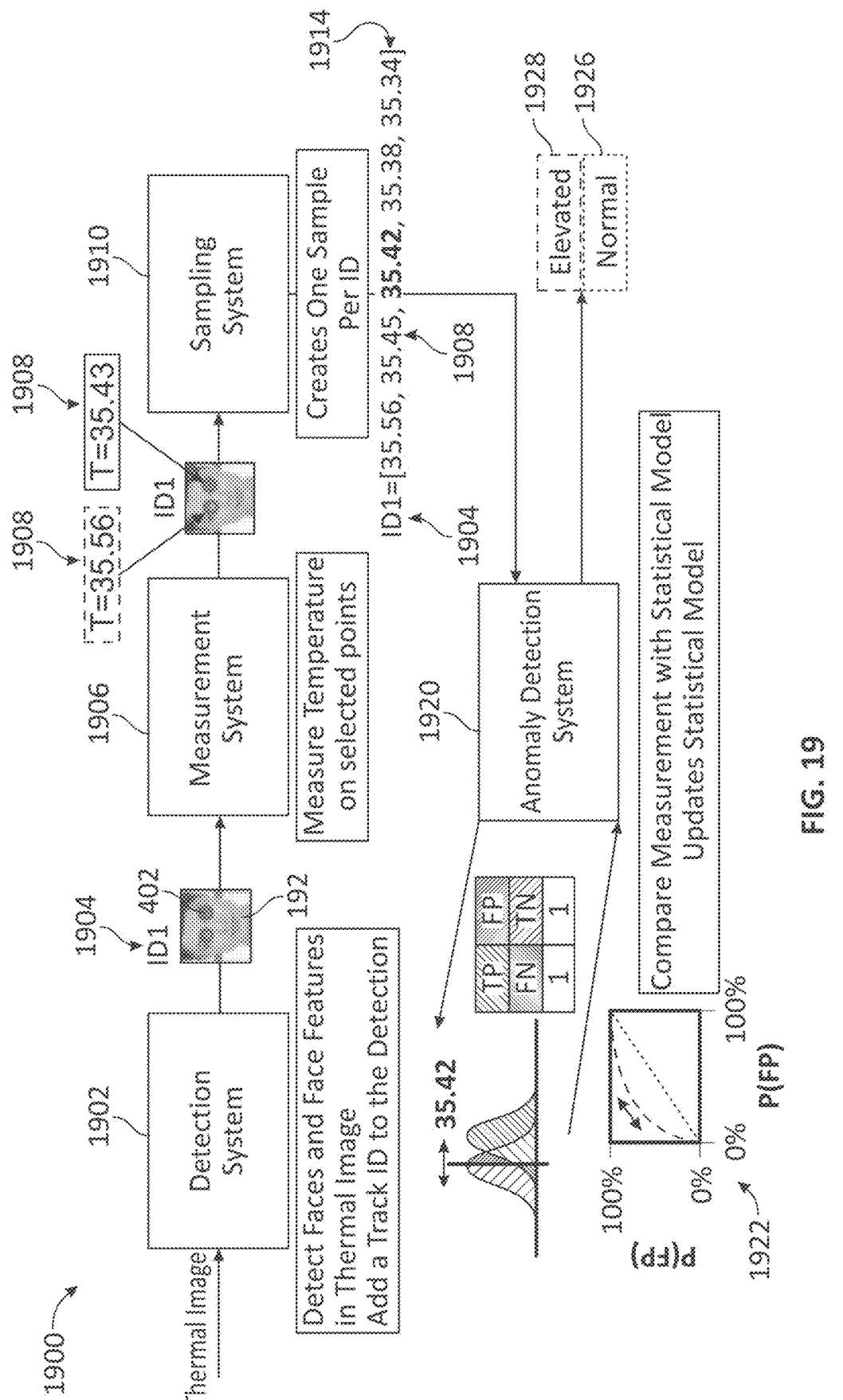
FIG. 19 illustrates a workflow of determining whether a human being has an elevated or normal temperature using a statistical model in accordance with an embodiment of the disclosure.

FIG. 19 illustrates a workflow 1900 performed by system 100 to determine whether a human being has an elevated or normal temperature using a statistical model in accordance with an embodiment of the disclosure. Workflow 1900 provides a method of updating a statistical model and providing a resulting elevated or normal temperature determination, indicating whether human being 192 has an elevated temperature compared to previous samples. Workflow 1900 may be performed in block 1247 of FIG. 12.

As shown, one or more thermal images (e.g., as captured by thermal imager 164, such as in block 1215 of FIG. 12) may be provided to a detection system 1902. The detection system 1902 may be a module or program running on logic device 168 and/or other logic device of system 100. Detection system 1902 may detect one or more faces and/or facial features in the thermal image(s). For example, detection system 1902 may detect and highlight the inner canthus 402 of human being 192 within the thermal image(s). In embodiments, detection system 1902 may detect a face covering (e.g., mask 1310) worn by human being 192 (e.g., using neural network 300). In embodiments, detection system 1902 may process the thermal images in block 1220 of FIG. 12. Detection system 1902 may add a track ID 1904 to the detection (e.g., "ID01" as shown).

The output of detection system 1902 (e.g. thermal image(s) with track ID 1904) may be provided to a measurement system 1906. Like detection system 1902, measurement system 1906 may be a module or program running on logic device 168 and/or other logic device of system 100. Measurement system 1906 may determine a temperature measurement 1908 on selected points of the thermal image (s). For example, measurement system 1906 may determine the temperature measurement 1908 of the inner canthus 402 of human being 192 using corresponding pixels of the thermal image, such as described above, such as in block 1233 of FIG. 12. Measurement system 1906 may determine and/or apply a correction term to the temperature measurement 1908 (e.g., prior to the detecting) to compensate for attenuation associated with the face covering 1310, such as in block 1235 and/or block 1240 of FIG. 12. In some embodiments, measurement system 1906 may determine a body temperature of human being 192 using the temperature measurement 1908.

The output of measurement system 1906 (e.g., thermal image(s) with track ID 1904 and measured temperature(s) 1908) may be provided to a sampling system 1910. Sampling system 1910 may be a module or program running on logic device 168 and/or other logic device of system 100. Sampling system 1910 may create one sample 1914 per track ID 1904. For example, sample 1914 may include the track ID 1904 and the measured temperature(s) 1908.

The sample 1914 may be provided to an anomaly detection system 1920. Anomaly detection system 1920 may be a module or program running on logic device 168 and/or other logic device of system 100. The anomaly detection system 1920 may process (e.g., compare) the measured temperature(s) 1908 with a statistical model 1922, such as in block 1247 of FIG. 12. If the measured temperature(s) 1908 is/are within a threshold of statistical model 1922, the temperature of human being 192 is determined to be normal (e.g., at block 1250 of FIG. 12). If, however, the measured temperature(s) 1908 is/are higher than the statistical model 1922, the temperature of human being 192 is determined to be elevated (e.g., at block 1250 of FIG. 12).

The statistical model 1922 may be any mathematical model that embodies one or more statistical assumptions concerning canthus temperature measurements. A normal temperature determination may be based on the one or more measured temperatures 1908 exceeding a threshold (e.g., exceeding a threshold probability). An elevated temperature determination may be based on the one or more measured temperatures 1908 exceeding or falling below a threshold (e.g., below a threshold probability).

As discussed with regard to block 1255 of FIG. 12, one or more notifications may be generated to identify an elevated body temperature in response to the body temperature exceeding a threshold. For example, the normal temperature determination may be provided at notification 1926 (e.g., fifth notification 1700). The elevated temperature determination may be provided at notification 1928 (e.g., sixth notification 1800). Notifications 1926 and 1928 may be provided on display 178, a user interface, or other device. In embodiments, an elevated temperature determination may trigger an alarm and/or a request for appropriate follow-up procedure. For instance, a secondary measurement method may be triggered to determine whether human being 192 is running a fever.

The statistical model 1922 may be dynamic. For example, each time a face is within the appropriate distance for measurement, the measured inner canthus region temperature (e.g., measured temperature of inner canthus 402) may be added to the statistical model 1922 to provide a running average. The running average may be kept from all previous canthus temperature measurements to identify an above-average temperature. For example, if the measured inner canthus region temperature is higher than the current running average, an elevated temperature determination may be made.

Where applicable, various embodiments provided by the present disclosure can be implemented using hardware, software, or combinations of hardware and software. Also, where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as program code and/or data, can be stored on one or more computer readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the present invention. Accordingly, the scope of the invention is defined only by the following claims.

What is claimed is:

1. A method comprising:
 capturing a thermal image of a human being using a thermal imager;

determining an uncompensated temperature measurement associated with an inner canthus of a face of the human being using corresponding pixels of the thermal image;
 preprocessing a plurality of initial thermal images of a plurality of subjects to determine one or more fitting constants based on a correlation between a distance and a face width of each of the plurality of subjects;
 determining a correction term as a function of the one or more fitting constants and the distance between the thermal imager and the human being, wherein determining the correction term includes determining a number of pixels of the thermal image associated with a width of the face; and
 applying the correction term to the uncompensated temperature measurement to provide a corrected temperature measurement associated with the inner canthus to compensate for attenuation associated with the distance.

2. The method of claim 1, further comprising:
 determining the distance using a predetermined association between the number of pixels and the distance.

3. The method of claim 1, wherein the width of the face comprises an ear-to-ear width.

4. The method of claim 1, further comprising detecting the face of the human being and the inner canthus in the thermal image.

5. The method of claim 4, wherein the detecting comprises processing the thermal image by an artificial neural network.

6. The method of claim 1, further comprising:
 determining, using a statistical model, a threshold based on a running average of a determined body temperature; and
 determining an elevated body temperature of the human being using the corrected temperature measurement by determining if the corrected temperature measurement exceeds the threshold.

7. The method of claim 6, further comprising generating a notification to inform a user of the thermal imager of the elevated body temperature.

8. The method of claim 1, further comprising repeating the method for a plurality of human beings at a plurality of distances from the thermal imager.

9. The method of claim 1, wherein the method is performed by a portable thermal camera comprising the thermal imager.

10. The method of claim 1, further comprising:
 detecting a face covering worn by the human being;
 determining one or more properties of the face covering, wherein the one or more properties comprise type, color, material, and/or position of the face covering relative to the inner canthus; and
 determining the correction term as a function of the one or more properties of the face covering.

11. A system comprising:
 a thermal imager; and
 a logic device configured to:
 operate the thermal imager to capture a thermal image of a human being,
 determine an uncompensated temperature measurement associated with an inner canthus of a face of the human being using corresponding pixels of the thermal image,
 preprocess a plurality of initial thermal images of a plurality of subjects to determine one or more fitting constants based on a correlation between a distance and a face width of each of the plurality of subjects;

determine a correction term as a function of the one or more fitting constants and the distance between the thermal imager and the human being, wherein determining the correction term includes determining a number of pixels of the thermal image associated with a width of the face, and apply the correction term to the uncompensated temperature measurement to provide a corrected temperature measurement associated with the inner canthus to compensate for attenuation associated with the distance.

12. The system of claim 11, wherein the logic device is configured to:

determine the distance using a predetermined association between the number of pixels and the distance.

13. The system of claim 11, wherein the width of the face comprises an ear-to-ear width.

14. The system of claim 11, wherein the logic device is configured to detect the face of the human being and the inner canthus in the thermal image.

15. The system of claim 14, wherein the logic device is configured to process the thermal image by an artificial neural network to detect the face and the inner canthus.

16. The system of claim 11, wherein the logic device is configured to:

determine, using a statistical model, a threshold based on a running average of a determined body temperature; and determine an elevated body temperature of the human being using the corrected temperature measurement by determining if the corrected temperature measurement exceeds the threshold.

17. The system of claim 16, wherein the logic device is configured to generate a notification to inform a user of the thermal imager of the elevated body temperature.

18. The system of claim 11, wherein the logic device is configured to determine corrected temperature measurements for a plurality of human beings at a plurality of distances from the thermal imager.

19. The system of claim 11, wherein the system is a portable thermal camera.

20. The system of claim 11, wherein the logic device is configured to:

detect a face covering worn by the human being;

determine one or more properties of the face covering, wherein the one or more properties comprise type, color, material, and/or position of the face covering relative to the inner canthus; and determine the correction term as a function of the one or more properties of the face covering.

\* \* \* \* \*